United States Patent [19]

Brun et al.

[11] 4,354,406
[45] Oct. 19, 1982

[54] METHOD OF AND DEVICE FOR FORMING OPENINGS IN A GELATINOUS SUBSTANCE

[75] Inventors: Alain Brun, Pavillons sous Bois; Louis Marcotte, Chevilly la rue Rungis; Béla Szarazi, Paris, all of France

[73] Assignee: L'Oreal, Paris, France

[21] Appl. No.: 224,501

[22] Filed: Jan. 13, 1981

[30] Foreign Application Priority Data

Jan. 14, 1980 [FR] France .............................. 80 00693

[51] Int. Cl.³ .............................................. B26F 1/00
[52] U.S. Cl. .......................................... 83/24; 83/55; 83/100; 83/167; 83/562; 83/569
[58] Field of Search ................... 83/24, 100, 167, 569, 83/562, 701, 50, 55

[56] References Cited

U.S. PATENT DOCUMENTS

| 2,463,455 | 3/1949 | Dann | 83/879 X |
| 3,600,772 | 8/1971 | Farris | 83/167 |
| 3,683,736 | 8/1972 | Loose | 83/701 X |
| 3,863,353 | 2/1975 | Hurn | 83/169 X |

*Primary Examiner*—James M. Meister
*Attorney, Agent, or Firm*—N. Jerome Rudy

[57] ABSTRACT

A method and device for forming openings in a gelatinous substance in a Petri dish in which the Petri dish (6) is lifted towards punch tools (19) until the tools have penetrated the gelatinous substance and are on or near the base of the dish. The dish is then moved with a low amplitude motion perpendicular to the penetration direction, i.e. horizontally to loosen a pellet of the gelatinous substance within each punch tool from the base (6a) of the dish, and finally the dish is lowered to withdraw the punch tools (19) from the dish while suction applied to a compartment (4) communicating with the interior of each tool extracts the punched pellet and clears the tool for a subsequent penetration in the same or a different dish (6).

17 Claims, 6 Drawing Figures

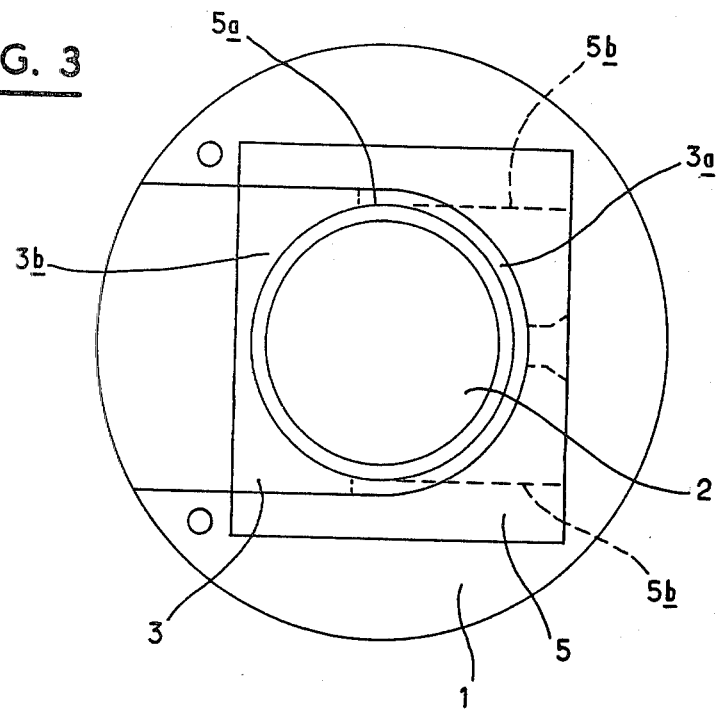
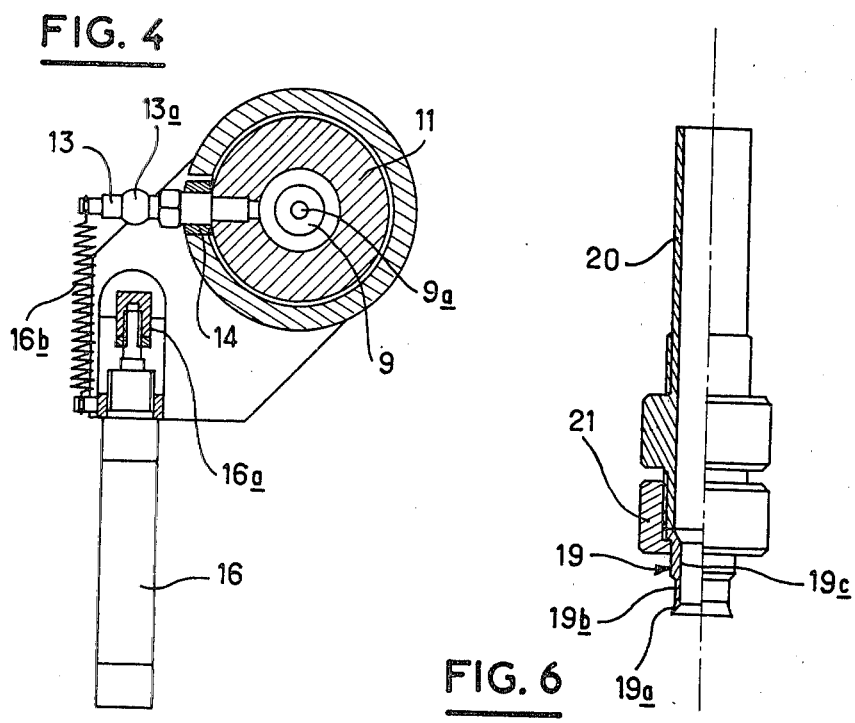

METHOD OF AND DEVICE FOR FORMING OPENINGS IN A GELATINOUS SUBSTANCE

The present invention relates to a method of, and a device for, making holes or openings in a gelatinous substance and in particular, in the gelose of a Petri dish.

It is known that in bacteriological laboratories, it is usual to cut out holes or openings in gelose or other gelatinous substances intended for cultures, capable of receiving for instance, liquid substances intended for diffusion purposes. These openings are at present obtained manually by means of punch tools. It follows in particular, that the shape of these openings is not always perfect and that their arrangement in the Petri dish is not regular which entails drawbacks, in particular for the measurements and experiments which are to be effected by means of these dishes. Moreover, obtaining these openings does constitute a tedious task in the laboratories and one which increases the laboratory working costs.

It is an object of the present invention to provide a method for making openings in gelatinous material, and gelose in particular, which would make it possible to obtain in this substance openings of perfect geometry and constant dimensions which would, moreover, both allow the openings to be arranged in the dish in a regular manner and lend itself to operation at a high rate capable of being semi-automated or entirely automated. The invention also proposes to obtain a device of a simple and low cost design allowing this method to be implemented under economic conditions.

Accordingly the present invention provides a method of forming openings in a gelatinous substance, comprising the steps of: causing a hollow punch tool to penetrate the gelatinous substance perpendicularly to the surface and to the bottom of the gelatinous substance along a strictly rectilinear path along the axis of the tool; when the tool has arrived at or near the bottom, effecting at least one relative motion of low amplitude between the gelatinous substance and the tool in a direction substantially perpendicular to the path of penetration; and then one withdrawing the gelose pellet cut out within the hollow tool.

The relative motion between the gelatinous substance and the punch tool may be obtained by means of a forward and backward travel or a forward and backward rotation around an axis displaced from the tool axis or yet again by vibrations in the transverse plane to the tool axis with a low frequency and adequate amplitude.

The speed of penetration of the tool into the gelatinous substance such as gelose may be determined experimentally. Generally, speeds of the order of 50 mm per second prove convenient. The exit trajectory of the tool is along the track of the entry trajectory, the exit speed of the tool out of the gelose is preferably greater than, and advantageously at least double, the speed of penetration.

The amplitude of the lateral displacement must be sufficiently small so as not to cause the gelose surrounding the tool to be destroyed. This amplitude may, for instance, be below 2 mm, and preferably of the order of 1 mm.

One may, in accordance with the method according to the invention, use one or several punch tools to obtain several openings at one time. Thus one may advantageously use two or three tools and in the frequent case where it is desired to obtain a greater number of openings in a Petri dish, for instance, six openings, there will be effected after each penetration and withdrawal phase, a relative rotation between the tools and the Petri dish of the angle necessary to obtain a uniform distribution of the openings.

The invention also provides a device for forming openings in a gelatinous substance, comprising at least one hollow punch tool; a support for a receptacle containing the gelatinous substance; means for causing said at least one punch tool to penetrate into the gelatinous substance in said receptacle along a rectilinear path with a given amplitude and then withdrawal of the tool along the same path; means for producing a low amplitude relative motion in a transverse direction in relation to the path of penetration of the punch tool or tools; and means for extracting the gelatinous substance cut out within the or each said tool.

In a preferred embodiment, the tool is fixed and the support for the receptacle containing the gelatinous substance, for instance the Petri dish, is mounted in a sliding manner so as to approach the tool and then to withdraw therefrom, the said support being, moreover, capable of being subjected to a short reciprocating motion in a transverse direction in relation to the tool axis.

Preferably, especially for an evacuation by way of suction, the tool has, in its effective part penetrating into the gelose, a cylindrical shape followed by a downwardly divergent cutting edge so as to leave a small passage between the wall of the formed opening and the external surface of the tool.

In a particular embodiment, the tool or tools which take the general shape of hollow elongated cylinders, are fixed to the bottom part of a suction compartment wherein they open via their top end, provision being made for means of suction or the production of a partial vacuum to establish low pressure in the suction compartment, capable of ensuring the extraction of the pellet of the gelatinous substance cut out from within the tool, the pellets progressively accumulating in the suction compartment.

In a particularly preferred embodiment, wherein the receptacles are displaced towards the punch tool or tools, the receptacle such as the Petri dish is maintained within a cylindrical guide component, preferably having a side opening for introducing the receptacle which rests on a sliding component towards the tool or tools, more preferably by means of a very flexible elastic coupling so as to prevent the risk of a sudden contact between the tool end and the bottom of the dish. Preferably, the transverse movement imparted to the receptacle is rotational and in this case, provision may advantageously be made for the sliding support to be mounted rotatably around its axis, the base of the receptacle being temporarily fixed to the said support, for instance by establishing suction within this coupling.

Thus the support may take the shape of a sliding component guided in a cylindrical guide and actuated by the end of the piston rod of a ram, the said component comprising a central channel for establishing the suction within the coupling which surmounts the component, the component having moreover a radial element capable of sustaining, when the component is in the high position, the action of a displacement means producing a rotation of the component around the rod axis. This means of displacement may advantageously be obtained by means of a further ram having a very short travel, the element or radial arm subjected to the thrust of the further ram being capable of being returned by a spring into its initial position.

In a particularly advantageous way, the component may be guided in a cylindrical guide and the radial arm passes through the said guide by means of a slot whose two edges form the end stops for the transverse rotational movement.

In order that the invention may more readily be understood, the following description is given as a non-restrictive example, with reference to the accompanying drawings, in which:

FIG. 3 is a top plan view of the guiding component of this device;

FIG. 4 is a cross-sectional view along line 4—4 of FIG. 1;

FIG. 6 shows an enlarged axial cross-sectional view of a punch tool of the device.

Figure 1:
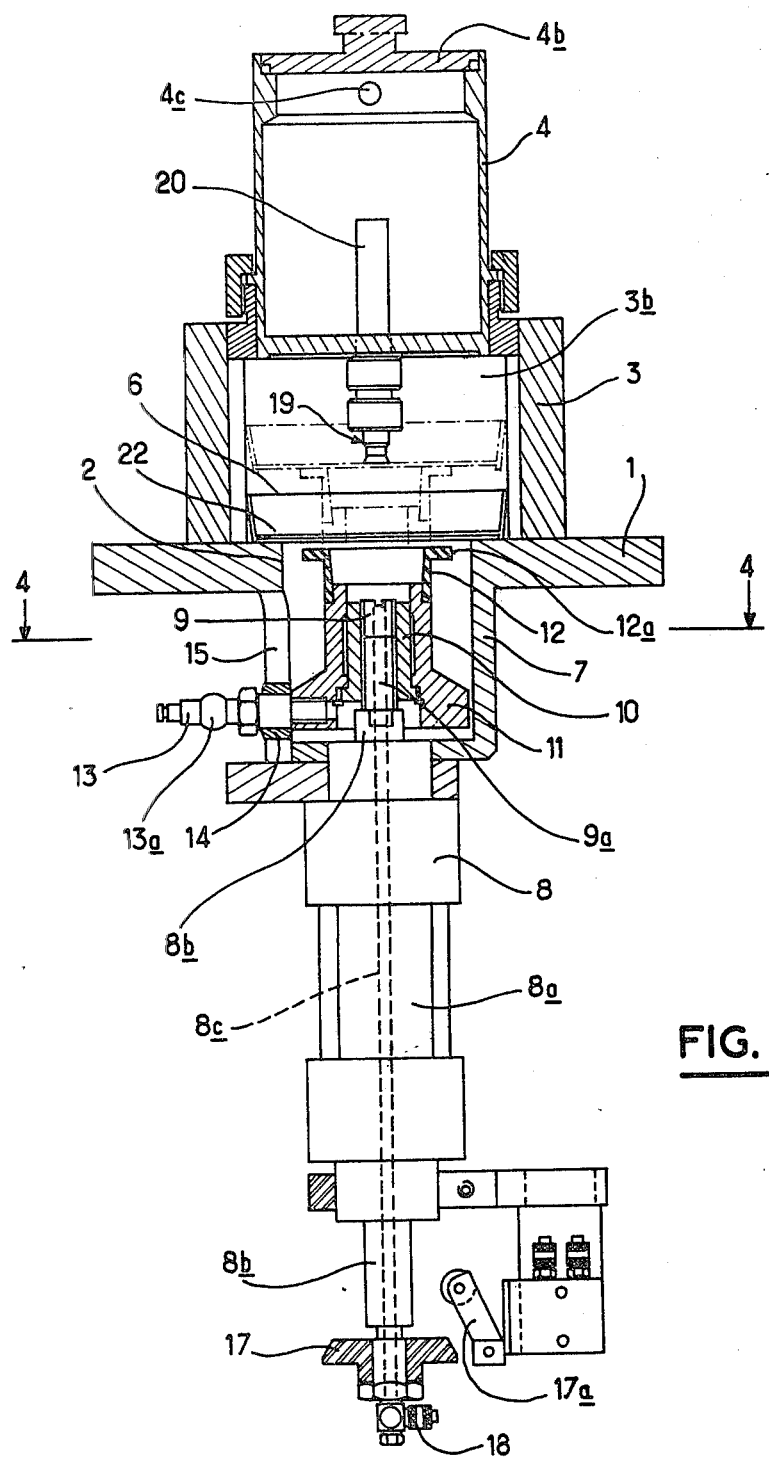
FIG. 1 is an axial cross-sectional view of one embodiment of a device according to the invention.
Figure 2:
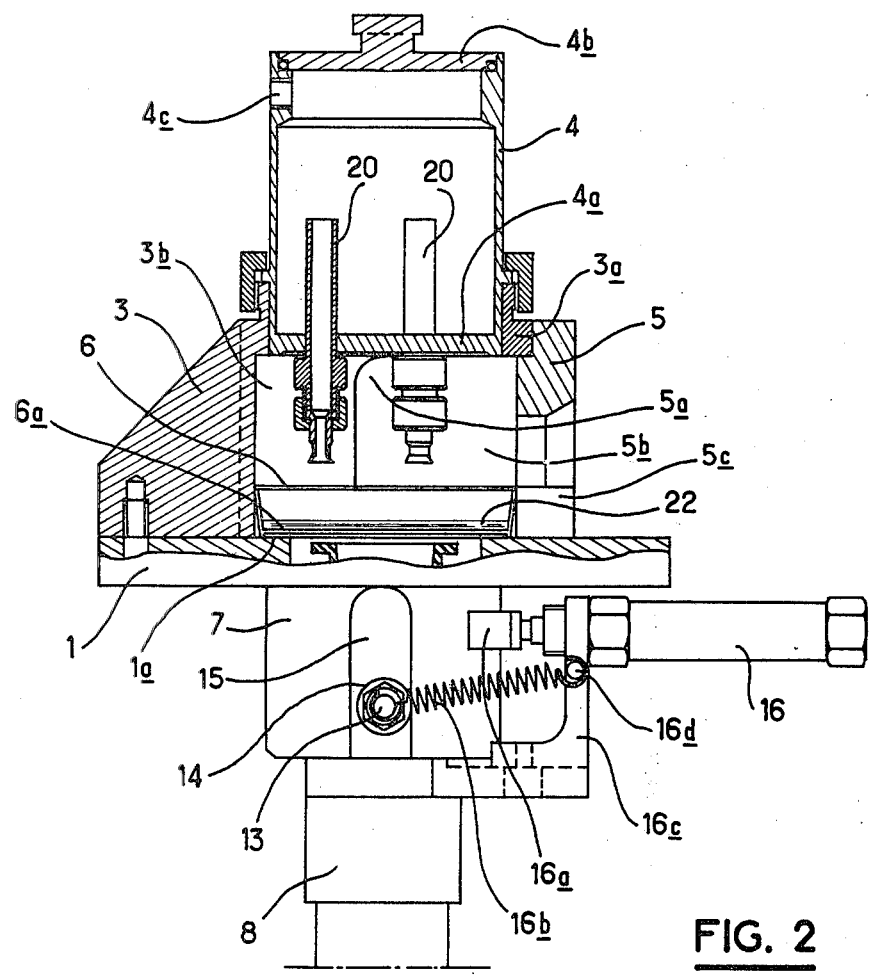
FIG. 2 is an axial cross-sectional view, displaced by 90° from that of FIG. 1, and showing the top part of this device.

The device shown in the drawing comprises a fixed plate 1 provided with a central opening 2 (FIG. 3), on which plate there is fixed a guide component 3 provided with an upper part having a cantilevered centre portion 3a provided with a passage which is coaxial with opening 2 and receives the bottom part 4a of a compartment 4 obturated at its top end by a lid 4b and provided with a lateral suction orifice 4c. Below the cantilevered portion 3a, the component 3 has a cylindrical internal wall 3b which is completed by a corresponding internal side wall 5a of a component 5 which is capable of sliding between the plate 1 and the cantilevered portion 3a to its position where the cylindrical walls 3b and 5a are concentric. The surfaces 5a of component 5 are extended by parallel planar surfaces 5b, and a lower passage 5c is provided within component 5 and has a width slightly greater than that of a Petri dish 6 to allow the dish 6 to be introduced via passage 5c. Sliding the dish 6 along lower passage 5c enables it to be positioned within the seating thus formed when the circumference of dish 6 comes into contact with the cylindrical surface 3b. In this position, the Petri dish 6 rests via its bottom 6a on a ledge 1a formed by plate 1 around the periphery of passage 2.

Figure 5:
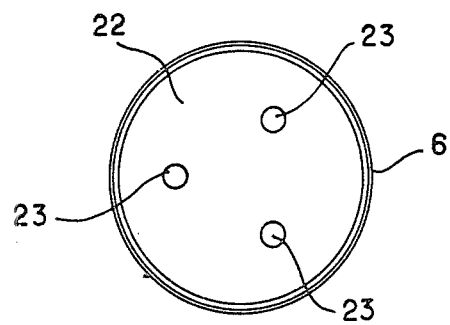
FIG. 5 is a top plan view of an arrangement of the openings in the Petri dish.

Bottom 4a of compartment 4 has three passages through which pass the punch tools 20 regularly spaced around the axis of the compartment and orifice 2. In this case there are three punch tools spaced at intervals of 120° as seen, for instance, in FIG. 5. The detailed structure of each punch tool 20 is shown in FIG. 6.

Around the passage 2 the plate 1 extends downwardly via an extension in the shape of a sleeve 7 against the bottom of which there is arranged a ram 8 whose cylinder 8a is traversed by a continuous piston rod 8b provided with a central through-bore 8c. The top end of piston rod 8b is extended by a threaded rod 9 around which there is screwed a component 10, carrying a freely rotatable but axially fixed sleeve component 11 which has at its top a generally cylindrical cup 12 of a very flexible rubber, terminating in an upper flange 12a intended to contact the base 6a of Petri dish 6. The interior of the cup communicates with the through-bore 8c via a central channel 9a in the cylindrical rod 9.

Into the base of sleeve component 11 which is enlarged on its outside, there is screwed the end of a radial arm 13 carrying a roller 14 arranged in a longitudinal slot 15 of the downward extension sleeve 7. At the end of arm 14, there is attached a helical tension spring 16b whose other end is fixed at 16d on a bracket 16c supporting a horizontal arm 16 whose piston rod carries a head 16a capable of contacting a bulging part 13a of arm 13 when the arm 13 is in the high position.

At the bottom of piston rod 8b, there is fixed the circular base plate 17 having a bevelled periphery capable of actuating a limit switch 17a.

Finally, right at the bottom of the piston rod 8b is a tube connector 18 enabling through-bore 8c and hence, through the intermediary of passage 9a, the interior of the flexible cup 12 to be subjected to suction by means of a flexible pipe, not shown.

The punch tool 19 shown in more detail in FIG. 6 has, starting from the bottom and working upwardly, a cutting edge 19a which is obliquely downwardly divergent, a recessed cylindrical portion 19b and a thicker cylindrical portion 19c terminating in a small external flange, allowing it to be clamped against the inner face of a tubular component 20 by means of a nut 21. The tubular component 20 sealingly engages over a long length with the interior of compartment 4 within which interior a sub-atmospheric pressure of from 100 to 200 mm of mercury is established by means of a pump which is not shown. This arrangement of the punch tool 19 allows rapid dismantling for sterlisation or replacement.

The functioning of the device is as follows:

The Petri dish containing gelose 22 is introduced via passage 5c into the guide assembly formed by components 3 and 5, the piston rod 8b of ram 8 being at this instant in the lowered position as shown in the drawing so that the flange 12a of flexible cup 12 is withdrawn below bearing 1 which supports base 6a of the Petri dish 6. Once the Petri dish 6 is in position, ram 8 is actuated to raise its piston 8b at a speed of 50 mm per second. When flange 12a of the cup 12 comes into contact with base 6a of the Petri dish, it lifts the dish and simultaneously, by virtue of the low air pressure (i.e. suction) obtained along passage 8c, it holds the dish 6 (which is further guided by faces 3b and 5a) in position on the cup 12 to which the dish thus becomes fixed. At the end of a certain time, the punch tools 19 carried by the three rods 20 penetrate into the gelose 22, which is approximately 4 mm thick, and there they cut out the openings so that the substance previously filling the opening forms a pellet now disposed within the tool 19. The travel of the ram piston rod 8a is continued until the cutting edge 19a of each tool 19 has come into contact with the base 6a of the Petri dish, the flexibility of suction cup 12 allowing an unduly high impact loading of the tools on the bottom to be prevented, so that the impact may thus be limited, for example to 100 g. As from this moment when sleeve component 11 and hence arm 13 are brought into the top position, the horizontal ram 16 is actuated so that its head 16a comes into contact with the rounded zone 13a of arm 13 which is then pushed in a clockwise direction (as viewed in FIG. 4) by the head 16a so that sleeve component 11 pivots around component 10 communicating its rotation to the dish 6 itself via suction cup 12 on which the Petri dish is now held. This rotation of less than one second's duration is effected from the initial position shown in FIG. 4 where the roller 14 is held by the tension spring 16b in contact with one of the edges of the slot 15, along an angular travel of approximately 1° which is terminated by the arrest and then the return of head 16a before the roller 14 has reached the other edge of slot 15. The return into the initial position is ensured by tension spring 16b.

This small angular rotation is sufficient to produce the complete separation of the pellet of the substance contained within tool 19 and has the effect of detaching the bottom of this gelose pellet from the base of the Petri dish, thus releasing the pellet which can, by the application of suction to the suction orifice 4c, then be drawn into the interior of the tubular component 20 and hence into compartment 4 where it remains stored. It should be noted that, probably by reason of the external structure of the punch tool 19 in relation to the surface of the thus created opening, the pellet contained within any one punch tool 19 will still be sucked out even if the pellets contained in the two other punch tools 19 have already been previously drawn off.

After this operation, ram 8 is activated so as to produce the downward return of piston rod 8b at twice the speed of its ascent thus producing the descent of dish 6 still attached to suction cup 12 by the action of the low pressure maintained within the cup; therefore the tool is progressively withdrawn out of the formed opening 23. At the end of a certain lapse of time, the base 6a of Petri dish 6 finds itself supported on ledge 1a whilst the continued descent of the ram piston rod 8b does in the end produce the separation of suction cup 12 from base 6a.

The piston rod of the ram 8 then returns to its bottom position shown in the drawing, and the Petri dish 6 may then be withdrawn by horizontal sliding along passage 5c and be replaced by a new one.

If, instead of the three openings 23, it is desired to obtain six openings in the dish, it is sufficient to subject the dish 6 to a rotation of 60° (i.e. one half of the angular interval between the three punch tools). It will, however, be understood that it would also be possible to make sleeve component 11 in such a way that its top could be rotated in relation to its bottom through an angle of 60° by means of devices which are within the expert's reach.

By way of example we can indicate that it has been possible, using a device according to the invention, to effect the setting up of the openings in 4 seconds, that is to say, one second for the ascent and descent and a pause of two seconds to reinstate the low pressures to the desired value.

The invention is of course amenable to various variants within the expert's reach, both as regards the methods and the device. Thus provision may be made for means allowing the opening, the positioning, and then the closing of the Petri dish to be effected automatically to ensure complete automation. Moreover, instead of being fixed against rotation, the tools could be mounted on a turret.

We claim:

1. A method of forming openings in a gelatinous substance, comprising the steps of: causing a hollow punch tool to penetrate the gelatinous substance perpendicularly to the surface and to the bottom of the gelatinous substance along a strictly rectilinear path along the axis of the tool; when the tool has arrived at least near the bottom effecting relative motion of low amplitude between the gelatinous substance and the tool in a direction substantially perpendicular to the path of penetration; and then withdrawing the pellet cut out from within the hollow tool.

2. A method according to claim 1, wherein the gelose pellet is extracted from the hollow tool by suction.

3. A method according to claim 1, wherein the said low amplitude relative motion is obtained by means of a translational movement.

4. A method according to claim 1, wherein said low amplitude relative motion is obtained by means of a rotation around an axis spaced from the tool axis.

5. A method according to claim 1, wherein said low amplitude relative motion is obtained by means of low frequency vibrations.

6. A method according to any one of claims 1 to 5, wherein the speed of penetration of the tool into the gelatinous substance is of the order of 50 mm per second, and the exit speed is higher.

7. A method according to claim 6, wherein said exit speed is at least double the speed of penetration.

8. A method according to any one of claims 1 to 5, wherein the amplitude of the low amplitude relative motion is less than 2 mm.

9. A method according to any one of claims 1 to 5, wherein in order to obtain a great number of openings, several tool penetrations are effected with a relative rotation between the tools and the gelatinous substance between two successive penetrations.

10. Device for forming openings in a gelatinous substance, comprising hollow punch tool means; a support for a receptacle containing the gelatinous substance; means for causing the said punch tool means to penetrate into the gelatinous substance in said receptacle along a rectilinear path with a given amplitude and then withdrawal of the punch tool means along the same path; means for producing a low amplitude relative motion in a transverse direction in relation to the path of penetration of the punch tool means; and means for extracting the gelatinous substance cut out within said punch tool means.

11. A device according to claim 10, wherein said punch tool means is mounted in a fixed position, the receptacle support is movable to approach the punch tool means and then withdraw therefrom, and said receptacle support is capable of a low amplitude reciprocating motion in a transverse direction in relation to the penetration path of the punch tool means.

12. A device according to claim 10, wherein said punch tool means comprises at least one vertical punch tool which has in its part intended to penetrate into the gelatinous substance, a cylindrical portion terminating at a downwardly divergent cutting edge which leaves a small passage between the wall of the formed opening and the external surface of the tool.

13. A device according to claim 10, including a suction compartment, and suction means effective to establish a low pressure within said suction compartment, and wherein said punch tool means comprise at least one hollow tool which has the general shape of an elongate hollow cylinder fixed to the bottom of said suction compartment with the interior of said at least one tool communicating with said suction compartment whereby suction in said compartment ensures the extraction of the pellet of gelatinous substance cut out by said at least one tool.

14. A device according to claim 12 or 13, wherein said at least one punch tool is mounted in a fixed position; said receptacle support is movable to approach the said at least one punch tool and then withdraw therefrom, and is adapted to perform a low amplitude reciprocating motion in a transverse direction relative to the axis of said at least one tool; and wherein said device further includes means defining a cylindrical inner guide surface and a lateral opening for introducing a receptacle.

15. A device according to any one of claims 10 to 13, wherein said receptacle support is constituted by a flexible elastic coupling.

16. A device according to any one of claims 10 to 13, wherein said receptacle support includes suction means for establishing a low pressure under the base of said receptacle to fix the receptacle temporarily to said support.

17. A device according to claim 16, wherein said receptacle support comprises a flexible elastic coupling, first ram means having a piston rod, a component rotatably supporting said coupling on said piston rod, means defining a suction passage within said piston rod, suction means effective to establish a low pressure within said suction passage and said coupling, a radial arm to said component rotatably supporting said coupling, means defining a longitudinal slot within which said arms is guided for executing a certain angular deflection, second ram means for pivoting said arm about the axis of rotation of said component, and spring means for effecting return pivoting of said arm when said first ram means has its piston rod extended to a position close to the punch tool means.

* * * * *